US00PP19107P2

(12) United States Plant Patent
Zary

(10) Patent No.: US PP19,107 P2
(45) Date of Patent: Aug. 19, 2008

(54) HYBRID TEA ROSE PLANT NAMED 'JACSEGRA'

(50) Latin Name: *Rosa hybrida*
Varietal Denomination: JACsegra

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 11/585,435

(22) Filed: Oct. 23, 2006

(51) Int. Cl.
*A01H 5/00* (2006.01)

(52) U.S. Cl. ..... Plt./133

(58) Field of Classification Search ..... Plt./133
See application file for complete search history.

*Primary Examiner*—Kent L. Bell
*Assistant Examiner*—S. B. McCormick-Ewoldt
(74) *Attorney, Agent, or Firm*—Klarquist Sparkman, LLP

(57) ABSTRACT

Hybrid tea rose plant having clear white, well-formed flowers; very strong fragrance; long vase life; strong, upright growth; dark green, healthy foliage; and ability to root easily and also grow vigorously with the aid of an understock.

1 Drawing Sheet

Figure 1:
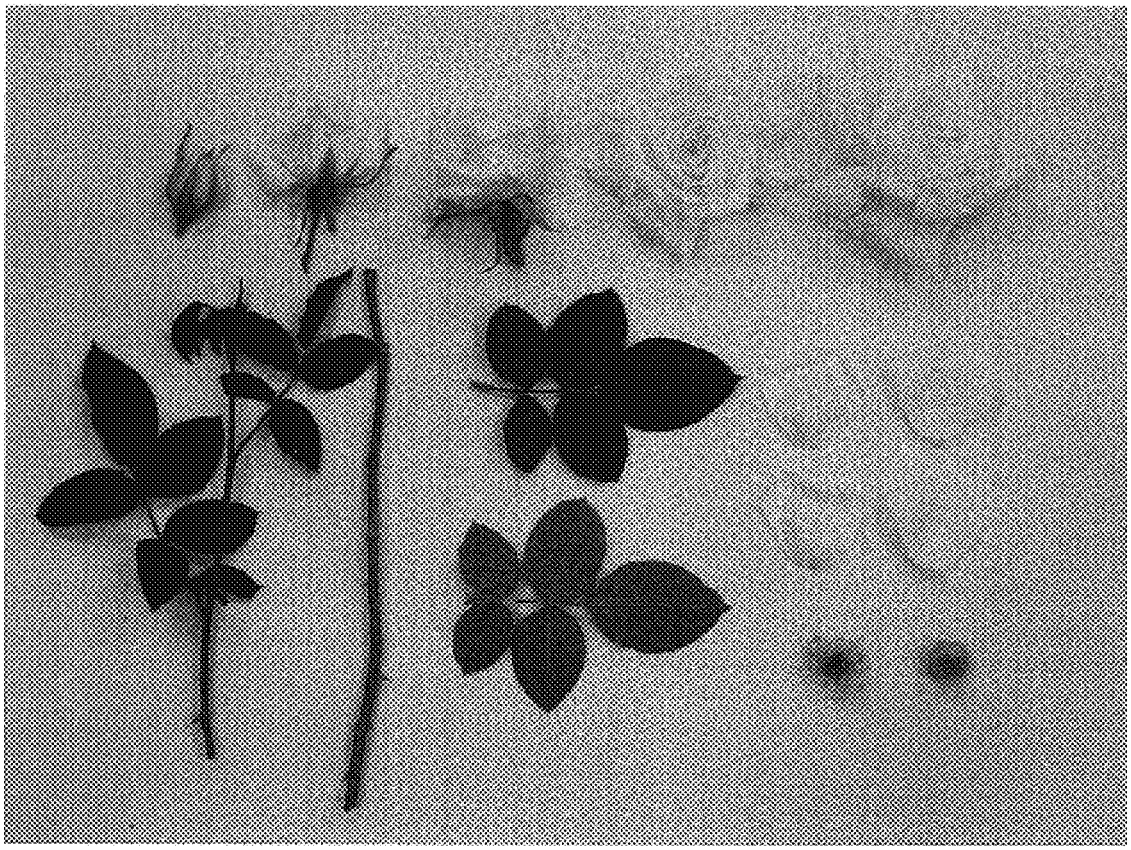

Genus and species: *Rosa hybrida.*
Variety denomination: 'JACsegra'.

ORIGIN OF THE INVENTION

The present invention relates to a new and distinct variety of a hybrid tea rose plant named 'JACsegra' which was originated by me by crossing the variety 'HILaroma' (Secret) (U.S. Plant Pat. No. 8,494) with the variety 'JACsee' (Fragrant Lace) (U.S. Plant Pat. No. 11,138).

BACKGROUND OF THE INVENTION

The primary objective of this breeding was to produce a new hybrid tea rose variety having the strong fragrance and wonderful flower form of the female parent combined with the strong fragrance and strong disease resistant foliage of the male parent.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Clear white, well-formed flowers.
2. Very strong citrus fragrance.
3. Long vase life.
4. Strong, upright growth.
5. Dark green, healthy foliage.
6. Ability to root easily and also to grow vigorously with the aid of an understock.

Asexual reproduction of this new variety by cuttings, as performed at Wasco and Somis, Calif., shows that the foregoing and all other characteristics and distinctions come true to form and are established and transmitted through succeeding propagations.

Comparison with Parents

'JACsegra' differs from the female parent in flower color (pink versus white) and in flower size (12-13 cm versus 15 cm for 'JACsegra'). 'JACsegra' differs from the male parent in flower color (light pink versus white) and in open flower form (the center of the flower has many petals and petaloids for 'JACsee' versus imbricated for 'JACsegra').

Comparison with Similar Variety

'JACsegra' differs from other white hybrid teas by its powerful fragrance and the strong resistance to fungal diseases found in 'JACsegra'. The closest hybrid teas are 'JAColite' (expired U.S. Plant Pat. No. 4,167) and 'MACl-anoflon' (believed unpatented).

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart© 2001, except where ordinary dictionary significance of color is indicated.

Parentage:

*Seed parent.*—'HILaroma' (Secret) (U.S. Plant Pat. No. 8,494).

*Pollen parent.*—'JACsee' (Fragrant Lace) (U.S. Plant Pat. No. 11,138).

FLOWER

Observations made from January 2006 to October 2006 from plants commencing at two years of age grown in a garden environment at Somis, Calif.

Blooming habit: Continuous.

Bud:

*Size.*—About 35 mm long and 25 mm in diameter when the petals start to unfurl.

*Form.*—The bud form is long, pointed ovoid.

*Color.*—When sepals first divide, bud color is a blend of Green-White Group 157D. When half blown, the upper and lower sides of the petals are White Group 155C.

*Sepals.*—Color: Upper surface: Green Group 138C. Lower surface: Yellow-Green Group 146C. Length: 22-25 mm. Width: 9-11 mm. Shape: Subulate. Surface texture: Hoary. There are three lightly to normally appendaged sepals. There are two unappendaged sepals with hairy edges.

*Receptacle.*—Color: Yellow-Green Group 146B. Shape: Funnel. Size: Large, about 20 mm wide×10 mm long. Surface: Smooth.

*Peduncle.*—Length: Short, averaging about 50-60 mm. Surface: Smooth, with just a few glands. Color: Yellow-Green Group 146B. Strength: Stiff, erect, heavy.

Bloom:

*Size.*—Large. Average open diameter is about 14-15 cm.

*Borne.*—Singly.

*Stems.*—Strength: Strong. Average length is about 40-46 cm with a diameter of 6-8 mm.

*Form.*—When first open: High centered. Permanence: Retains its form to the end, outer petals curl back, quill fashion.

*Petalage.*—Number of petals under normal conditions: 45-50.

*Color.*—The upper sides of the petals are White Group 157D. The reverse sides of the petals are White Group 157D. The bases of the petals have a Yellow Group 8B spot, 10 mm wide×5 mm deep, on both surfaces of the petal. The major color on the upper sides is White Group 157D.

*Discoloration.*—The general tonality at the end of the first day: No change. At the end of the third day: No change.

*Fragrance.*—Strong, citrus.

Petals:

*Texture.*—Thick.

*Surface.*—Smooth.

*Shape.*—Round.

*Margin.*—Entire. Apex Shape: Rounded. Base Shape: Rounded.

*Form.*—Tips slightly recurved, moderately quilled.

*Arrangement.*—Imbricated.

*Petaloids.*—Number: 3 to 7. Size: Range from 3-7 mm wide×10 mm long to 15 mm wide to 20 mm long. Color: White Group 157D.

*Persistence.*—Petals drop off cleanly before drying.

*Lastingness.*—On the plant: Long (about 5-7 days). As a cut flower: Long (about 8-9 days).

Reproductive parts:

*Stamens.*—Number: 85-95. Length: 7-8 mm. Anthers: Length: 3 mm. Color: Yellow-Orange Group 18B. Arrangement: Regular around styles, mixed with petaloids. Filaments: Color: Green-White Group 157A. Length: 4-5 mm. Pollen: Color: Greyed-Orange Group 163A.

*Pistils.*—Number: 100-115. Length: 7-8 mm. Styles: Color: Greyed-Purple Group 185A. Length: 6-7 mm. Stigmas: Color: Orange-White Group 159A. Length: 1 mm.

*Hips.*—None observed.

PLANT

*Form.*—Bush.

*Growth.*—Vigorous, upright, branching.

*Age at maturity.*—Two years.

*Mature plant.*—Height: 1.7 m-1.8 m. Width: 1.2 m-1.3 m.

*Rootstock.*—Own root.

Foliage: Number of leaflets on normal mid-stem leaves: 5 or 7.

*Size.*—Large. About 130 mm long×100 mm wide.

*Quantity.*—Abundant.

*Color.*—New foliage: Upper side: Greyed-Purple Group 183A. Lower side: Greyed-Purple Group 183C. Old foliage: Upper side: Green Group 139A. Lower side: Yellow-Green Group 147C.

Leaflets:

*Size.*—About 45 mm long×35 mm wide.

*Shape.*—Pointed oval.

*Base shape.*—Rounded.

*Apex shape.*—Acuminate.

*Texture.*—Leathery, glossy.

*Edge.*—Serrated.

*Serrations.*—Single.

*Petiole.*—Color: Yellow-Green Group 146D.

*Petiole rachis.*—Color: Yellow-Green Group 146D. Underside: Smooth with occasional prickles.

*Auricles.*—None.

*Stipules.*—Length: 13-14 mm; smooth with some glands; Number: 2; color of upper and lower surfaces, Yellow-Green Group 146D.

*Disease resistance.*—Resistant to rust and mildew under normal growing conditions and susceptible to blackspot, but very tolerant.

*Pest resistance.*—Not observed.

*Vein color.*—Yellow-Green Group 147C.

*Venation pattern.*—Reticulate.

Wood:

*New wood.*—Color: Greyed-Purple Group 183B. Bark: Smooth.

*Old wood.*—Color: Green Group 137C. Bark: Smooth.

Prickles:

*Quantity.*—On main canes from base: Ordinary to few (8-10 per 15 cm of stem). On laterals from main canes: None.

*Form.*—Hooked downward.

*Length.*—7-10 mm.

*Color when young.*—Greyed-Purple Group 183B.

*Color when mature.*—Greyed-Orange Group 165A.

Small prickles:

*Quantity.*—On main stalks: None. On laterals: None.

Winter hardiness: Hardy to Zone 5.

I claim:

1. A new and distinct variety of rose plant of the hybrid tea class, substantially as herein shown and described, characterized particularly by its clear white, well-formed flowers; very strong fragrance; long vase life; strong, upright growth; dark green, healthy foliage; and ability to root easily and also to grow vigorously with the aid of an understock.

* * * * *